United States Patent [19]
Ried et al.

[11] Patent Number: 5,919,624
[45] Date of Patent: Jul. 6, 1999

[54] METHODS FOR DETECTING CERVICAL CANCER

[75] Inventors: Thomas Ried, Bethesda, Md.; Gert Auer, Solna, Sweden; Evelin Schröck, Rockville, Md.; Kerstin Heselmeyer, Edewecht, Germany; Merryn Macville, Kensington, Md.

[73] Assignee: The United States of America as represented by the Department of Health & Human Services, Washington, D.C.

[21] Appl. No.: 08/781,424

[22] Filed: Jan. 10, 1997

[51] Int. Cl.⁶ .............................. C12Q 1/68; C12P 19/34; C07H 21/04; C07H 21/02
[52] U.S. Cl. .......................... 435/6; 435/91.2; 536/23.1; 536/24.31; 935/77; 935/78
[58] Field of Search ...................... 435/6, 91.2; 536/23.1, 536/24.31; 935/77, 78

[56] References Cited

PUBLICATIONS

Atkin NB, Baker MC, Fox MF (1990) Chromosome changes in 43 carcinomas of the cervix uteri. *Cancer Genet Cytogenet* 44:229–241.

Fearon ER, Vogelstein B (1990) A genetic model for colorectal carcinogenesis. *Cell* 61:759–767.

Isola J, DeVries S, Chu L, Ghazrini S, Waldman F (1994) Analysis of changes in DNA sequence copy number by comparative genomic hybridization in archival paraffin–embedded tumor samples. *Am J Pathol* 145:1301–1308.

Kallioniemi A, Kallioniemi O–P, Sudar D, Rutovitz D, Gray JW, Waldman F, Pinkel D (1992) Comparative genomic hybridization for molecular cytogenetic analysis of solid tumors. *Science* 258:818–821.

Kallioniemi A, Kallioniemi O–P, Piper J, Tanner M, Stokke T, Chen L, Smith HS, Pinkel D, Gray JW, Waldman FM (1994) Detection and mapping of amplified DNA sequences in breast cancer by comparative genomic hybridization. *Proc Natl Acad Sci USA* 91:2156–2160.

Mitra AB, Murty VV, Singh V, Li RG, Pratap M, Sodhani P, Luthra UK, Chaganti RS (1995) Genetic alterations at 5p15: a potential marker for progression. *J Natl Cancer Inst* 87:742–745.

(List continued on next page.)

*Primary Examiner*—Stephanie Zitomer
*Attorney, Agent, or Firm*—Needle & Rosenberg, P.C.

[57] ABSTRACT

The invention provides a method of detecting the presence of invasive cervical carcinoma in a subject comprising detecting in a cervical cell from the subject the presence of a chromosome abnormality which is associated with invasive cervical carcinoma; the presence of the cervical cell containing the chromosome abnormality indicating the presence of invasive cervical carcinoma in the subject. The invention also provides a method of detecting the presence of advanced-stage cervical carcinoma in a subject comprising detecting in a cervical cell from the subject the presence of a chromosome abnormality associated with advanced-stage cervical carcinoma; the presence of the cervical cell containing the chromosome abnormality indicating the presence of advanced-stage cervical carcinoma in the subject. The invention also provides a method of classifying the progression of dysplastic cervical cells from a non-invasive cervical carcinoma to an invasive cervical carcinoma comprising analyzing the dysplastic cervical cells for the presence of a chromosome abnormality which is associated with invasive cervical carcinoma, and classifying the dysplastic cervical cells having the chromosome abnormality as having progressed from a non-invasive cervical carcinoma cells to an invasive cervical carcinoma. The invention further provides kits comprising nucleic acids that specifically hybridize to chromosome 3q and specifically hybridize to another chromosome, and to compositions comprising nucleic acids.

7 Claims, 6 Drawing Sheets

OTHER PUBLICATIONS

Mullokandov MR, Kholodilov NG, Atkin NB, Burk RD, Johnson AB, Klinger HP (1996) Genomic alterations in cervical carcinoma: losses of chromosomal heterozygosity and human papilloma virus tumor status. *Cancer Res* 56:197–205.

Popescu NC, DiPaolo JA (1992) Cytogenetics of cervical neoplasia. *Cancer Genet Cytogenet* 60:214–215.

Ried T, Just KE, Holtgreve–Grez H, du Manoir S, Speicher MR, Schröck E, Latham C, Blegen H, Zetterberg A, Cremer T, Auer G (1995) Comparative genomic hybridization of formalin fixed, paraffin embedded breast carcinomas reveals different patterns of chromosomal gains and losses in fibroadenomas and diploid and aneuploid carcinomas. *Cancer Res* 55:5415–5423.

Ried T, Knutzen R, Steinbeck R, Blegen H, Schröck E, Heselmeyer K, du Manoir S, Auer G (1996) Comparative genomic hybridization reveals a specific pattern of chromosomal gains and losses during the genesis of colorectal tumors. *Genes Chromosom Cancer* 15:234–245.

Ried T, Veldman T, Heselmeyer K, du Manoir S, Shah K, Auer G, Schrock E. (1996) Molecular cytogenetic analysis of cervical tumors reveals a gain of chromosome 3q as a genetic marker of progression (Meeting abstract) *Proc Ann Meet Am Assoc Cancer Res*; 37:A1290.

Srivatsan ES, Misra BC, Venugopalan M, Wilczynski SP (1991) Loss of heterozygosity for alleles on chromosome 11 in cervical carcinoma. *Am J Hum Genet* 49:868–877.

Steinbeck RG, Heselmeyer K, Moberger H, Auer G (1995) The relationship between proliferating cell nuclear antigen (PCNA), nuclear DNA content and mutant p53 during genesis of cervical carcinoma. *Acta Oncol* 34:171–176.

Zur Hausen H (1994) Disrupted dichotomous intracellular control of human papillomavirus infection in cancer of the cervix. *Lancet* 343:955–957.

| Case# | MIB (%) | DNA-Ploidy | HPV | CGH |
|---|---|---|---|---|
| 1 | 10 | 2.0c, D | neg. | / |
| 2 | 5 | 2.0c, D | neg. | / |
| 3 | 10 | 2.0c, D | neg. | / |

| Case# | MIB (%) | DNA-Ploidy | HPV | CGH |
|---|---|---|---|---|
| 1 | 10 | 3.9c, T | n.d. | +18p,-X |
| 2 | 15 | 3.8c, T | neg. | / |
| 3 | 10 | 3.8c, T | n.d. | -X |
| 4 | 20 | 4.1c, T | neg. | -X |

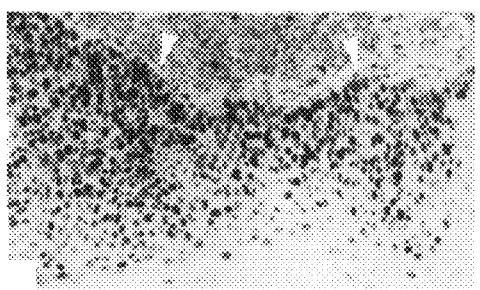
| Case# | MIB (%) | DNA-Ploidy | HPV | CGH | |
|---|---|---|---|---|---|
| 1 | 40 | 4.7c, A | n.d. | +18p | |
| 2 | n.d. | 4.1c, T | neg. | / | |
| 3 | 30 | 4.1c, T | n.d. | / | FIG.1C |
| 4 | n.d. | 4.3c, A | neg. | -X | |
| 5 | 40 | 4.1c, T | n.d. | -X | |
| 6 | 30 | | 58 | / | |
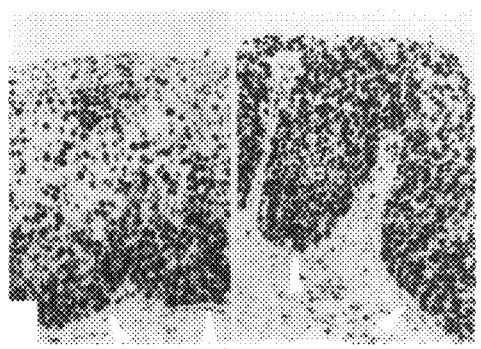
| Case# | MIB (%) | DNA-Ploidy | HPV | CGH | |
|---|---|---|---|---|---|
| 1 | 90 | 3.8c, A | 16 | / | |
| 2 | 85 | 3.8c, T | 16 | / | |
| 3 | 50 | 4.4c, T | n.d. | / | |
| 4 | 90 | 4.0c, A | 16 | / | |
| 5 | 80 | 5.0c, A | 58 | / | |
| 6 | 85 | 3.6c, A | 33 | -X | |
| 7 | 80 | 4.1c, A | 16 | / | FIG.1D |
| 8 | 90 | 4.1c, A | 33 | / | |
| 9 | n.d. | 3.6c, A | 58 | -X | |
| 10 | n.d. | 3.8c, T | 16 | / | |
| 11 | 80 | 3.9c, A | generic | +18p | |
| 12 | 90 | 3.7c, A | 16 | +3q,-3p22-24 | |
| 13 | n.d. | 4.0c, T | 16 | / | |

| Case# | MIB (%) | DNA-Ploidy | HPV | CGH |
|---|---|---|---|---|
| 1 | 90 | 4.8c, A | 16 | +3q,-4q,-13q21-qter |
| 2 | 95 | 5.0c, A | 45 | +1q,+2p,+3q22-qter, +6p,-6q,+9q,-11p |
| 3 | 90 | 4.2c, A | 16 | +3q,-13q21,-Xp |
| 4 | 50 | 4.0c, T | 18 | / |
| 5 | 85 | 5.0c, A | 16 | +3q,+5p,-3p,-6q, -X |
| 6 | 80 | 4.0c, A | generic | +3q,-10,-11q14-qter |
| 7 | 90 | 3.9c, A | 16 | +3q,-4q22-qter,-5q15-22 |
| 8 | 80 | 4.1c, A | 16 | +1,+3,+7,+9,+15,+17, +19,+21,+22 |
| 9 | 70 | 3.5c, A | 31 | +3q25-27,-3p,-X |
| 10 | 75 | 4.4c, A | neg. | +3q,-X |

METHODS FOR DETECTING CERVICAL CANCER

BACKGROUND OF THE INVENTION

1. Field of the Invention

This invention relates generally to methods of detecting the presence of a cervical carcinoma. Specifically, this invention relates to a method of detecting a cervical carcinoma by detecting the presence of a chromosome abnormality in a cervical cell that is associated with the cervical carcinoma.

2. Background Art

Cervical carcinomas are the second most common tumors in women worldwide. The tumor incidence shows strong variability, with industrialized countries having lower morbidity and mortality rates than do developing countries (*Pisani et al.* (1993) "Estimates of the worldwide mortality from eighteen major cancers in 1985. Implications for prevention and projections of future burden" Int J Cancer 55:891–903) which may be attributable to differences in cytologic screening programs (*Hakama et al.* (1986) "Screening for cancer of the uterine cervix" IARC Scientific Publications No. 76, Lyon, France). Although other factors, such as cigarette smoking, may influence the incidence of cervical cancer, infection with human papilloma virus (HPV) can be an initiating event for cervical carcinogenesis. (IARC Monograph, 1995). An HPV infection alone, however, is not sufficient for the progression of the disease from a stage of mild cellular dysplasia to a stage of invasive carcinoma since some HPV infected cervical cells may never progress to the more malignant stage, and in fact, may never progress past a stage of mild dysplasia. The traditional clinical diagnostic test for the presence of dysplastic cells, the Papanicolaou (Pap) smear, does not provide a reliable predictor of the progression of dysplastic cells to cancerous cells since this test is based upon morphological characteristics of the cells which do not reliably reflect the genetic state of the cells. Additionally, the Pap smear analysis is essentially a subjective test which is therefore susceptible to misinterpretation.

Polyploidy has been associated with the transition of normal cervical cells to dysplastic cervical cells, but this crude genetic determination has also not been associated with cells undergoing a transition past a stage of mild dysplasia other than showing a general increase in genetic instability. This genetic instability, as determined by monitoring ploidy levels, appears nonspecific to a particular chromosome and does not provide a correlation to the transition of dysplasia to invasive carcinoma. Therefore some additional process must occur for a transition of the dysplastic cervical cells to the more advances stages of the disease. It is conceivable that specific genetic aberrations are required for the multistep process of cervical cell tumor initiation and progression (*Fearon et al.* (1990) "A genetic model for colorectal carcinogenesis" Cell 61:759–767 and *Zur Hausen, H.* (1994) "Disrupted dichotomous intracellular control of human papilloma virus infection in cancer of the cervix" Lancet 343:955–957), but this association has never been discovered, and therefore, a relatively simple genetic determination of cervical cells in the more advanced stages of the disease, such as those entering into or already in the invasive stage, has not yet been possible.

Determination of mandatory genetic aberrations for tumor progression would lead to valuable diagnostic predictors. There is, therefore, a need for a method that can be used to readily detect the presence of a cancerous cervical cell that is independent of tests such as cytologic or morphologic appearance or overall ploidy levels.

The present invention solves this need by disclosing for the first time a method which allows the detection of a cancerous cervical cell by detecting a chromosome abnormality which is associated with a cervical carcinoma. Using this method, therefore, one can now detect the presence of a cancerous cervical cell in a population of cells which may be either HPV infected or polyploid, or both, and regardless of the morphological appearance of the cell or the cells ploidy level.

SUMMARY OF THE INVENTION

In accordance with the purpose(s) of this invention, as embodied and broadly described herein, this invention, in one aspect, provides a method of detecting the presence of invasive cervical carcinoma in a subject comprising detecting in a cervical cell from the subject the presence of a chromosome abnormality which is associated with invasive cervical carcinoma; the presence of the cervical cell containing the chromosome abnormality indicating the presence of invasive cervical carcinoma in the subject.

The invention further provides a method of detecting the presence of advanced-stage cervical carcinoma in a subject comprising detecting in a cervical cell from the subject the presence of a chromosome abnormality associated with advanced-stage cervical carcinoma; the presence of the cervical cell containing the chromosome abnormality indicating the presence of advanced-stage cervical carcinoma in the subject.

The invention also provides a method of classifying the progression of dysplastic cervical cells from a non-invasive cervical carcinoma to an invasive cervical carcinoma comprising analyzing the dysplastic cervical cells for the presence of a chromosome abnormality which is associated with invasive cervical carcinoma, and classifying the dysplastic cervical cells having the chromosome abnormality as having progressed from a non-invasive cervical carcinoma cells to an invasive cervical carcinoma.

The invention also provides kits comprising nucleic acids that specifically hybridize to chromosome $3q$ and to other chromosomes, and to compositions comprising nucleic acid probes.

BRIEF DESCRIPTION OF THE DRAWINGS

FIG. 1 shows the summary of the results from MIB-1 staining, DNA-ploidy measurements, HPV-genotyping, and CGH in cervical epithelial cells. FIG. 1C.: Moderate dysplasia (n=6); FIG. 1D.: Severe dysplasia/CIS (n=13)

DETAILED DESCRIPTION OF THE INVENTION

Figure 1A:
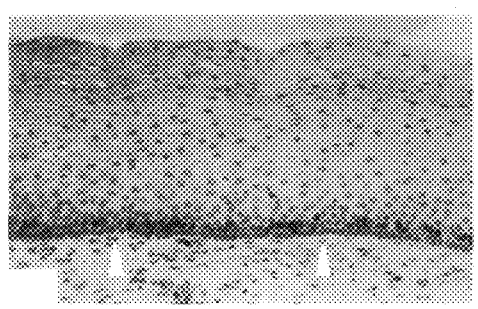
FIG. 1A.: Normal cervical epithelium (n=3)

The present invention may be understood more readily by reference to the following detailed description of the preferred embodiments of the invention and the Examples included therein and to the Figures and their previous and following description.

Before the present methods are disclosed and described, it is to be understood that this invention is not limited to specific cells, specific detection methods, or specific chromosome abnormalities, as such may, of course, vary, and the numerous modifications and variations therein will be apparent to those skilled in the art. It is also to be understood that the terminology used herein is for the purpose of describing particular embodiments only and is not intended to be limiting.

As used in the specification and in the claims, "a" can mean one or more, depending upon the context in which it is used. Thus, for example, reference to "a cervical cell" means that at least one cervical cell is utilized.

In one aspect, the invention provides a method of detecting the presence of invasive cervical carcinoma in a subject comprising detecting in a cervical cell from the subject the presence of a chromosome abnormality which is associated with invasive cervical carcinoma; the presence of the cervical cell containing the chromosome abnormality indicating the presence of invasive cervical carcinoma in the subject.

In another aspect, the invention provides a method of detecting the presence of advanced-stage cervical carcinoma in a subject comprising detecting in a cervical cell from the subject the presence of a chromosome abnormality associated with advanced-stage cervical carcinoma; the presence of the cervical cell containing the chromosome abnormality indicating the presence of advanced-stage cervical carcinoma in the subject.

The terms "invasive cervical carcinoma" and "advanced-stage cervical carcinoma" are terms familiar to one of ordinary skill in the art and are used herein to describe distinct stages or states in the progression of cervical cells from normal to preinvasive and invasive cancerous and further progressed stages. The first four states of this progression are often described as a cervical cell or cells progressing from a normal state to a state of mild dysplasia, followed by a state of moderate dysplasia, followed by a state of severe dysplasia/CIS (carcinoma in situ). These states are followed by a state of "invasive cervical carcinoma" where the cervical carcinoma cells can be described in at least three somewhat distinctive patterns: fungating (or exophytic), ulcerating, and infiltrative cancer, which are all spacially limited to the cervix tissues. "Advanced-stage cervical carcinomas" (Stage II–Stage IV) extend past this invasive but relatively confined stage and are typically characterized by their spread to surrounding structures including the peritoneum, urinary bladder, ureters, rectum, and vagina. (See, Cotran, et al. "Pathological Basis of Disease" W. B. Saunders Co., Philadelphia, Pa., 5th edition, pages 1048–1053).

One skilled in the art will appreciate that the precise method used to detect in a cervical cell the presence of a chromosome abnormality which is associated with invasive cervical carcinoma or an advanced-stage cervical carcinoma can, of course, vary. One such method which has been used to detect the presence of chromosome abnormalities is through simple visualization of stained metaphase chromosomes. Human chromosomes have distinct banding patterns and one skilled in the art can distinguish between the chromosomes on the basis of this banding pattern.

One skilled in the art will recognize that there are many assays based on visualization of the chromosome abnormality which can be used in the methods disclosed herein. For example, interphase in situ hybridization may be used to detect the presence of a chromosome abnormality which is associated with invasive cervical carcinoma or an advanced-stage cervical carcinoma. Interphase cytogenetics refers to the fact that chromosome aberrations can be analyzed directly in non-dividing cells, such as cytological preparations or in tissue sections. For instance, a trisomy 21 presents itself in metaphase chromosome of the specimen as three visible copies of this particular chromosome. A hybridization with a probe for chromosome 21 on the metaphase chromosome would highlight the three copies. The hybridization signal can be detected, for example, with fluorescent tags, or in a calorimetric format in which an absorbent color identifies the normal chromosome and the chromosome abnormality. In interphase cells, chromosomes have a morphology different than chromosomes in metaphase. The interphase chromosome, however, still maintains its organizational structure. Therefore hybridization of this interphase chromosome with a probe that recognizes chromosome 21 will highlight the additional chromosome by revealing an additional signal in the intact cells. Normal cells contain two copies; the super-numerary is indicated by three distinct spots. This approach, for example, can be used for screening of Pap smears with a chromosome-specific probe, such as a 3q probe, to detect the presence of an invasive cervical carcinoma. The acquisition of additional copies of at least a fragment of a chromosome or chromosome abnormality identified as associated with the progression of cervical carcinomas can be visualized directly in intact cells after the hybridization with a probe specific for selected chromosome or chromosome fragment. One advantage of such a test is that cells can be assayed directly from Pap smears since cell culture is not required. This type of assay, as well as other routine assays or detection procedures, can readily be automated to provide a sensitive genetic test that may be used to complement traditional assays for dysplasia/carcinoma such as the Pap smear.

Another method used to detect the presence of a chromosome abnormality associated with invasive cervical carcinoma or advanced-stage cervical carcinoma, and as disclosed in the Examples contained herein, comprises the use of comparative genomic hybridization (CGH). This test is based on selective hybridization of dual-color fluorescence in situ hybridization (FISH) using differentially labeled total tumor and reference DNA as probes. Copy number changes in tumor genomes versus control genomes are reflected in changes in the ratio of the two fluorochromes utilized. Once identified as aberrant in a particular tumor or a particular tumor stage, changes in specific chromosomes or even specific regions of chromosomes can be monitored by designing probes complementary to sequences on a particular chromosome or in a particular region of a chromosome using modified detection techniques.

The specific detection method used which is capable of detecting the presence of a chromosome abnormality which is associated with invasive cervical carcinoma or advanced-stage cervical carcinoma is, of course, not limited to visualization techniques. For example, the method may be based on amplification of at least a fragment of a chromosome which has an abnormality associated with invasive cervical carcinoma or advanced-stage cervical carcinoma. A detection method such as this may incorporate different detectable labels such as different radioisotopes into different locations in the genome to monitor the gain or loss of a particular region or regions. Therefore the detection method utilized may comprise nucleic acid amplification methods, such as the polymerase chain reaction (PCR). Therefore the methods disclosed herein can be performed not only in situ, but in vitro (for example with isolated DNA), or in vivo.

Alternatively, the detection method may comprise the use of chromosome or chromosome region-specific antibodies. These antibodies may bind directly to the chromosome or they bind to another molecule that is associated with a specific chromosome or a specific region of a chromosome. The present invention provides a method for detecting the presence of an invasive cervical carcinoma or an advanced-stage cervical carcinoma, by providing for the first time, the discovery that these carcinomas are associated with a specific chromosome abnormality, and the specific method or methods used to detect the chromosome abnormality are not limited to those exemplified herein.

The present invention, therefore, provides for the first time a reliable genetic test which can readily be used to monitor the progression of cervical cells from the dysplastic stages to the invasive cervical carcinoma stage, thereby detecting or classifying an invasive cervical carcinoma. This test is based on detecting in a cervical cell the presence of a chromosome abnormality which is associated with invasive cervical carcinoma. As disclosed and described in the Examples contained herein, the specific chromosome abnormality associated with an invasive cervical carcinoma comprises the presence of at least one extra copy of at least a fragment of chromosome 3q. The additional copy of at least a fragment of chromosome 3q may comprise a relatively small fragment of chromosome 3, such as 3q26–27 and 3q24–28 or the additional fragment may comprise an additional copy of the entire chromosome. Thus, "at least a fragment" includes a fragment of a chromosome or an intact chromosome.

The present invention further provides for the first time a reliable genetic test which can readily be used to monitor the progression of cervical cells from the dysplastic stages to an advanced-stage cervical carcinoma stage, thereby detecting the presence of an advanced-stage cervical carcinoma. This test is based on detecting in a cervical cell the presence of a chromosome abnormality which is associated with an advanced-stage cervical carcinoma. As disclosed and described in the Examples contained herein, a specific chromosome abnormality associated with an advanced-stage cervical carcinoma comprises the presence of at least one extra copy of at least a fragment of chromosome 5p, 1q, 6p, 8q, 15q, 17q, or 20. The additional copy of at least a fragment of chromosome 5p, 1q, 6p, 8q, 15q, 17q, or 20 may comprise a relatively small fragment of these chromosomes.

Alternatively, and as disclosed and described in the Examples contained herein, a specific chromosome abnormality associated with an advanced-stage cervical carcinoma may also comprise the loss of at least a fragment of chromosome 2q, 3p, 4p, 6p, 6q, 8p, 11q, or 13q.

The present invention also provides a method of classifying the progression of dysplastic cervical cells from a non-invasive cervical carcinoma to an invasive cervical carcinoma in a subject comprising analyzing the dysplastic cervical cells for the presence of a chromosome abnormality which is associated with invasive cervical carcinoma and classifying the dysplastic cervical cells having the chromosome abnormality as having progressed from a non-invasive cervical carcinoma cells to an invasive cervical carcinoma in the subject.

One of ordinary skill in the art will readily appreciate that the methods disclosed herein can be used to classify, identify, evaluate, grade, index, or otherwise indicate that dysplastic cervical cells are in an invasive cervical carcinogenic stage versus a non-invasive stage by detecting the presence of a chromosome abnormality which is associated with invasive cervical carcinoma. In one embodiment, the specific chromosome abnormality which is associated with the cervical cell having progressed from a non-invasive cervical carcinoma stage to an invasive cervical carcinoma stage is the presence of at least one extra copy of at least a fragment of chromosome 3q.

One of ordinary skill in the art will readily appreciate that the methods disclosed herein can be combined. For example, a method to detect the presence of chromosome 3q can be combined with a method or methods to detect the presence of any other chromosome or chromosome fragment, or a method or methods to detect the loss of at least a fragment of another chromosome.

The methods described herein can be used for detection of an invasive cervical carcinoma or an advanced-stage cervical carcinoma, or to classify the progression of dysplastic cervical cells from a non-invasive cervical carcinoma to an invasive cervical carcinoma in humans as well as any other subject. These methods may be practiced as in situ methods, in vitro methods, or in vivo methods. The present invention provides methods which can be used to detect the presence of invasive cervical carcinoma, methods which can be used to detect the presence of advanced-stage cervical carcinoma, and methods which can be used to classify the progression of dysplastic cervical cells from a non-invasive cervical carcinoma or non-invasive cervical carcinoma cells, and these methods are not limited to whether they are performed in situ, in vivo, or in vitro.

The present invention also provides a kit comprising a nucleic acid that specifically hybridizes to chromosome 3q and a nucleic acid that specifically hybridizes to a chromosome abnormality associated with advanced-stage cervical carcinoma. The chromosome abnormality may comprise the presence of at least one extra copy of at least a fragment of a chromosome selected from the group consisting of 5p, 1q, 6p, 8q, 15q, 17q, and 20. The chromosome abnormality may also comprise the loss of at least a fragment of a chromosome selected from the group consisting of 2q, 3p, 4p, 6p, 6q, 8p, 11q, and 13q.

Also provided by the present invention is a kit comprising a nucleic acid that specifically hybridizes to chromosome 3q and a nucleic acid that specifically binds to a chromosome other than 3q.

One of ordinary skill in the art will readily appreciate that these kits can comprise nucleic acid probes which specifically hybridize to a specific chromosome, and therefore can be used to detect the presence of or identify a specific chromosome or chromosomes or a fragment of a specific chromosome or chromosomes. These probes can be used in the methods described herein to detect the presence of an invasive cervical carcinoma or an advanced-stage cervical carcinoma, or both, and to classify the progression of a dysplastic cervical cell from a non-invasive cervical carcinoma to an invasive cervical carcinoma.

The invention also provides a composition comprising a nucleic acid that specifically hybridizes to chromosome 3q and a nucleic acid that specifically hybridizes to a chromosome abnormality associated with advanced-stage cervical carcinoma. This composition may comprises a nucleic acid that specifically hybridizes to chromosome 3q and a nucleic acid that specifically hybridizes to at least one chromosome selected from the group consisting of 5p, 1q, 6p, 8q, 15q, 17q, and 20. This composition may also comprise a nucleic acid that specifically hybridizes to chromosome 3q and a nucleic acid that specifically hybridizes to at least one chromosome selected from the group consisting of 2q, 3p, 4p, 6p, 6q, 8p, 11q, and 13q.

This invention also provides a composition comprising a nucleic acid that specifically hybridizes to chromosome 3q and a nucleic acid that specifically hybridizes to a chromosome other than 3q.

Throughout this application, various publications are referenced. The disclosures of these publications, and the references cited therein, in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and example be considered as exemplary only, with a true scope and spirit of the invention being indicated by the claims.

The following examples are set forth so as to provide those of ordinary skill in the art with a complete disclosure and description of how the methods claimed herein may be performed, and is intended to be purely exemplary of the invention and is not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in °C. and pressure is at or near atmospheric.

EXAMPLES

Gain of chromosome 3q defines the transition from severe dysplasia to invasive carcinoma of the uterine cervix We analyzed tissue from defined stages of cervical tumorigenesis utilizing a new molecular cytogenetic approach, termed comparative genomic hybridization (*Kallioniemi et al.* (1992) Science 258, 818–821 and *Du Manoir et al* (1993) Hum. Genet. 90, 590–610). Comparative genomic hybridization (CGH) serves as a screening test for DNA-copy number changes in tumor genomes. CGH is based on a two color fluorescence in situ hybridization, where a normal reference genome is labeled with a first fluorochrome (e.g. rhodamine) and genomic tumor DNA with a second fluorochrome, (e.g. fluorescein). After the hybridization of the differentially labeled genomes to normal reference metaphase chromosomes the changes in the ratio of the fluorescein/rhodamine intensities reflect DNA-copy number alterations in the tumor. Notably, genomic DNA is the only material from the tumor required for CGH-analysis, thus allowing the use of archived, formalin fixed and paraffin embedded samples as well (*Speicher et al.* (1993) Hum. Mol. Genet. 2, 1907–1914). In the present study, this unique feature of CGH was used to demonstrate the potential of the technique to create a phenotype/genotype correlation during the genesis of cervical neoplasia. Tumor DNA was extracted from microdissected regions of histological preparations, that were diagnosed on consecutive, hematoxylin/eosin (HE) stained sections. The same areas were analyzed for DNA-ploidy, proliferative activity, and the presence of HPV-genomes.

Materials and Methods

Tissue samples

The tumor material was collected between 1990 and 1994 from cervical biopsies or hysterectomies and diagnosed on HE-stained tissue sections at the Institute of Pathology, Flensburg, Germany, according to the World Health Organization (WHO) classification (*Poulsen et al.* (1975) WHO International histological classification of tumors, No. 13, Geneva). From each specimen 8 contiguous sections were prepared and used for histological diagnosis (thickness: 4 µm), immunohistochemistry (4 µm), DNA-ploidy measurements (8 µm), and microdissection (2×50 µm). Before and after each 50 µm sample 4 µm sections were cut for HE-staining. All data were obtained from the dissected areas.

Immunohistochemistry

Figure 1B:
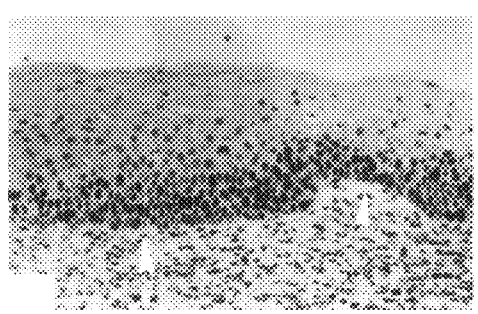
FIG. 1B.: Mild dysplasia (n=4)
Figure 1E:
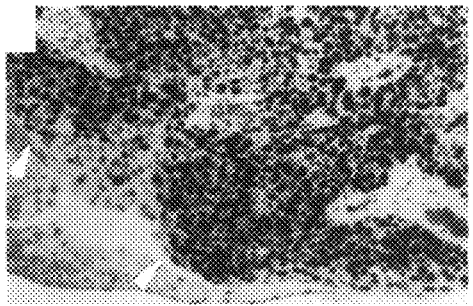
FIG. 1E.: Invasive carcinoma (n=10). The photographs in the left panel represent examples of staining patterns after incubation with the antibody MIB-1. The arrowheads indicate the region that was dissected from the slide. MIB-1 staining results are also presented as percentages of the cells that reacted positive with the antibody (row: MIB-1). The nuclear DNA-content in the tissues sections is presented in c-values, with $2c$ reflecting normal diploid DNA-content (row: DNA-ploidy). The histograms were classified as diploid (D), tetraploid (T), and aneuploid (A) (see also FIG. 2). The HPV-types are provided as determined by dot-blot analysis (row: HPV). Neg.: no detection of HPV-sequences; n.d.: not determined. The CGH-row shows the chromosomal aberrations detected in individual cases.

The monoclonal antibody MIB-1 (Immunotech S. A., Marseille, France, 1:150 in 1% BSA, visualized with the routine avidin-biotin-peroxidase complex technique) was used for the detection of the Ki-67 antigen on 4-mm-thick tissue sections (*Steinbeck et al.* (1995) Acta Oncologica 34, 171–175). The antibody discriminates non-proliferating (G0) cells from proliferating (G1-S-G2-M) cells. Any distinct nuclear MIB-1 staining was recorded as positive. Examples of the staining pattern and a quantification of the results are shown in FIG. 1.

DNA-cytometry

DNA-content measurements were performed using image cytometry on histological sections as described previously (*Steinbeck et al.* (1995) Acta Oncologica 34, 171–175 and *Auer et al.* (1989) Human Path. 20, 518–527). All DNA-values were expressed in relation to the corresponding staining controls which were given the value 2c, denoting the normal diploid DNA-content, and presented in such relative units. The specimens were divided into three main groups: (i) diploid cases with a distinct peak in the normal 2c region and no cells exceeding 5c, (ii) tetraploid cases with values in the 4c region and no or only a minor fraction of cells (<5%) exceeding 5c, and (iii) aneuploid cases with a main peak around the 4c region and varying numbers of cells (>5%) exceeding 5c. Examples of the histograms are presented in FIG. 2.

HPV-genotyping

HPV-genomes in the purified specimen DNA were identified by PCR using the MY09-MY11 L1 consensus primers for amplification (*Manos et al.* (1989) Molecular Diagnostics of Human Cancer: Cancer Cells, vol 7, ed. Furth, M., Greaves, M., (New York, Cold Spring Harbor Laboratory Press), p. 209). 25 type-specific and a generic HPV probe were used to diagnose the HPV-type in the PCR products as described in detail elsewhere (*Hildesheim et al.* (1994) J. Infect. Dis. 169, 235–240).

CGH analysis

Normal control DNA was prepared from peripheral blood lymphocytes of a cytogenetically normal male. Formalin fixed, deparaffinized and microdissected samples were provided in 50 µm thick tissue pieces stored in 95% ethanol. DNA preparation, labeling, and hybridization were performed. Briefly, 200 ng of normal, digoxigenin labeled DNA and 200 ng of biotin labeled tumor DNA were hybridized for 4 days and detected with fluorescein conjugated to avidin (Vector laboratories) and anti-digoxigenin Fab fragments conjugated to rhodamine (Boehringer Mannheim). Chromosomes were counterstained with DAPI (4; 6-diamidino-2-phenylindole), and embedded in an antifading agent to reduce photobleaching.

Microscopy and digital image analysis

Gray level images were acquired with a cooled charge coupled device (CCD) camera (Photometrics, Tucson, Ariz.) coupled to a Leica DMRBE epifluorescence microscope. Chromosomes were identified using DAPI-banding. Fluorescence ratio images were calculated as described and the ratio profiles of individual reference chromosomes were determined by a custom computer program (*Du Manoir et al.* (1995) Cytometry 19, 27–41) and run on a Macintosh Quadra 950.

Results

All invasive tumors analyzed were diagnosed as stage T1. The cellular DNA-content was assessed for all samples using image cytometry on Feulgen-stained tissue sections. A monoclonal antibody MIB-1) directed against the Ki-67 antigen was used to monitor proliferative activity in the cells present in the dissected areas. HPV genotyping was performed on the DNA used for CGH by consensus primer PCR and type specific dot-blot hybridization. FIG. 1 summarizes the results.

Normal epithelium, mild and moderate dysplasia

Figure 2A:
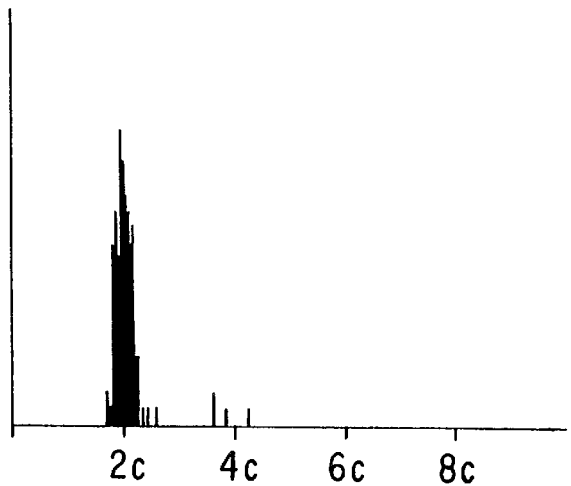
FIG. 2 shows DNA histograms displaying representative DNA-values in the diploid range (FIG. 2A), tetraploid range (FIG. 2B), and a scattered DNA-histogram with values exceeding 5c (FIG. 2C).
Figure 2B:
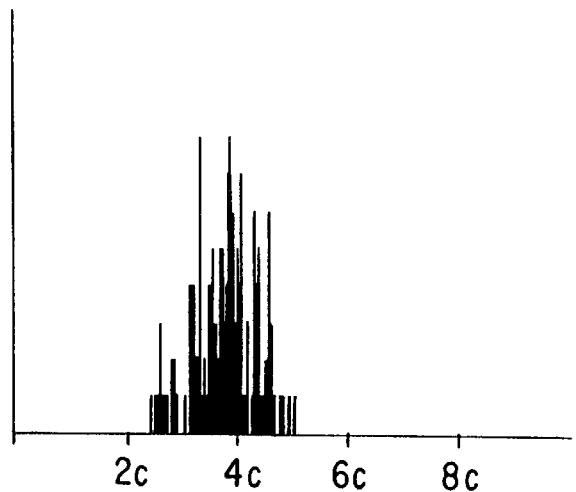
Figure 2C:
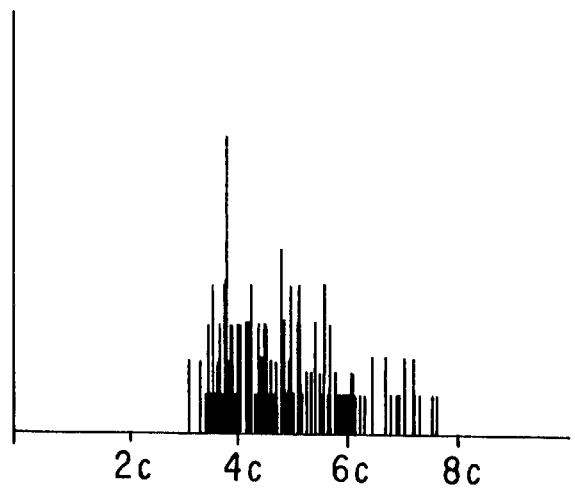

DNA was extracted from microdissected tissue of histomorphologically defined regions on consecutive sections of HE-stained slides of 13 cases of normal epithelium (n=3), mild dysplasia (n=4) and moderate dysplasia (n=6). None of the DNA extracted from the normal mucosa revealed the presence of HPV sequences. One of the two successfully tested mild dysplasias showed HPV 16 sequences, whereas HPV58 sequences were detected in one of 3 successfully tested cases of moderate dysplasia. The percentage of cells that stained positively with the proliferation marker MIB-1 was 5–10% in normal epithelium, 10–20% in mild dysplasia and 30–40% in moderate dysplasia. The cells in the normal cervical epithelium revealed a diploid DNA distribution (FIG. 2a). A peak fraction at 4c was visible in the majority of the tissues diagnosed as mild and moderate dysplasias. A representative DNA histogram (mild dysplasia, case #3) is shown in FIG. 2b. Except for the loss of the X chromosome, CGH did not reveal any recurrent copy number changes. In a single case of moderate dysplasia, a gain of the short arm of chromosome 18 was observed. See FIG. 1 for a summary of the results.

Severe dysplasia/CIS and invasive carcinoma

Figure 3:
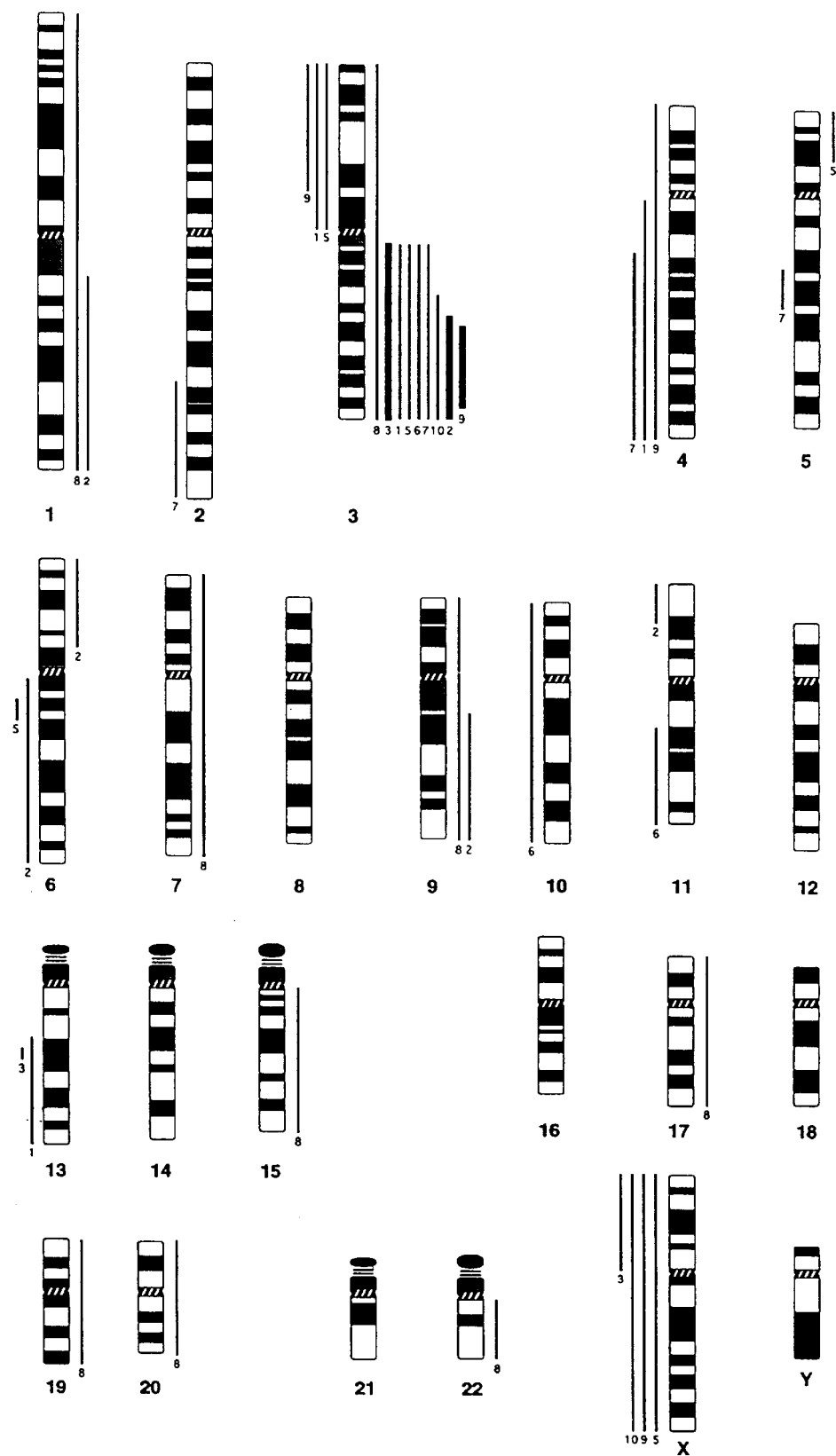
FIG. 3 shows the summary of the genetic imbalances detected in 10 primary invasive cervical carcinomas. Vertical lines on the left side of each chromosome ideogram represent loss of genetic material in the tumor, whereas those on the right side correspond to a gain. Changes in individual cases can be identified by the case number provided at the bottom of each line. High level copy number increases are represented as solid bars. The long arm of chromosome 3 was over represented in 9 of 10 cases. The consensus region on 3q that is gained in the carcinomas extends from band 3q24–28.

The PCR analysis of DNA extracted from severe dysplasias/CIS and carcinomas revealed invariably the presence of HPV genomes that are associated with cervical cancer, i.e., HPV16, 31, 33, 45, and 58. Immunoreactivity with MIB was detected in 50–95% of the cells of severe dysplasia/CIS and carcinoma, reflecting high proliferative activity. The tetraploid cell population that prevailed in the mild and moderate dysplasias shifted increasingly to aneuploid cell populations with scattered DNA values up to 8c, which indicates pronounced genetic instability in severe dysplasias/CIS and invasive carcinomas. An example of an aneuploid DNA histogram is presented in FIG. 2c. The results are summarized in FIG. 1. The CGH analysis of DNA extracted from severe dysplasias/CIS revealed only few specific chromosomal aberrations. In one case, loss of chromosome 3p was accompanied by a gain of chromosome 3q. Average ratio profiles were used for the identification of chromosomal imbalances in all cases analyzed in this study. The karyogram of chromosomal gains and losses of ten cases of carcinomas of the uterine cervix is displayed in FIG. 3. The number of chromosomal aberrations that were detected in invasive carcinomas using CGH was significantly higher compared to severe dysplasias/CIS. Losses of chromosomes or chromosomal subregions were observed in decreasing frequency on chromosome X, 3p, 4q, 6, 11, and 13q. In two often cases a gain of chromosome 1q and 9q was present. The most consistent finding in invasive cervical carcinomas was a gain of chromosome 3q, that was detectable in 9 of 10 cases. Notably, the gain of 3q was also observed as a high level copy number increase (amplification) in three cases. In two cases the ratio profile indicated a high level copy number increase only for a portion of 3q. The smallest region of overlap that was gained extended from chromosomal bands 3q24 to 3q28 (FIG. 3).

These results indicate that the gain of chromosome 3q is the most consistent chromosomal aberration in cervical carcinomas. This is the first study that has reported the recurrent gain of chromosome 3q in carcinomas of the cervix uteri. This aberration occurs during the progression from severe dysplasia/CIS to invasive carcinoma (stage T1) because only one of 13 severe dysplasias/CIS studied here showed an increase on 3q. The biological relevance of copy number increases on this chromosomal region in carcinomas is further underlined by the fact that high level copy number increases (amplifications) were found on 3q as well.

Chromosomal losses were found less frequently in this collection of cervical carcinomas: in three often cases chromosomes 3p and 4q are present in lower copy numbers. In one case of the carcinomas studied, 11q was subject to loss as well. Notably, the loss of 13q and 17p, the chromosomal arms that harbor the retinoblastoma (Rb) and p53 tumor suppressor genes, is rare in cervical carcinomas. This is in significant contrast to findings in other tumors, e.g. breast and lung cancers, studied by CGH (*Ried et al.* (1994) Cancer Res. 54, 1801–1806). A regional copy number decrease at the chromosomal map position of the retinoblastoma tumor suppressor gene (13q21) was observed in the carcinoma cases #1 and #3. However, HPV16 was present in the DNA extracted from both tumors, indicating that infection with HPV16 and deletion of the retinoblastoma tumor suppressor gene are not mutually exclusive.

The karyogram of chromosomal gains and losses in cervical carcinomas (FIG. 3) is remarkable in two aspects: (i) the number of chromosomal aberrations is relatively low; only 17 chromosomes are involved in gains or losses with an average number of chromosomal aberrations per tumor of 4.0. A significantly higher number of chromosomal aberrations was found in small cell lung cancers (23 chromosomes involved; average number of aberrations: 13.0 per tumor), glioblastomas (23; 9.2), and aneuploid breast cancers (19; 6.8) analyzed using CGH (Ried et al. (1994) Cancer Res. 54, 1801–1806 and Schröck et al. (1994). Am. J. Pathol. 144:1203–1218). (ii) High level copy number increases (amplifications), that were frequently observed in the above mentioned tumors on single chromosomal bands were rare in cervical carcinomas.

The data from this study indicates that the sequence of genetic events that result in the transition of normal cervical epithelium to dysplasias and finally invasive carcinomas consists of the following steps: (i) Tetraploidization is the first genetic abnormality, and occurs as early as in mildly dysplastic regions (Steinbeck et al. (1995) Acta Oncologica 34, 171–175). HPV-sequences were detected in half of the mildly and moderately dysplastic lesions. The proliferative activity, determined by MIB-1 staining, is elevated (and increases during progression). (ii) Severe dysplasias/CIS are almost invariably infected with high risk HPV-types. The tetraploidization as determined by DNA-content measurements persists, however, the cells reveal a pronounced genomic instability indicated by scattered DNA histograms that extend to 8c-values. (iii) In addition to high risk HPV-infection, aneuploidy, and high proliferative activity, the specific gain of chromosome 3q sequences is the most consistent chromosomal aberration, that becomes detectable when severely dysplastic cells have progressed to invasive cervical carcinomas (stage T1). Interphase FISH with 3q probes on tissue sections will allow therefore quantification of the cells that actually carry the gain of 3q and to determine their cellular origin.

Advanced-Stage Cervical Carcinomas are Defined by a Recurrent Pattern of Chromosomal Aberrations Revealing High Genetic Instability and a Consistent Gain of Chromosome Arm 3q In order to explore the relevance of the gain of chromosome arm 3q in advanced stages of tumor progression, and to identify additional copy number changes, CGH analysis was next performed on 30 cases of stage IIb to IV squamous cell carcinomas of the uterine cervix.

Materials and Methods

Tissue samples

Thirty tumors were collected at the Karolinska Hospital, Stockholm, Sweden, between 1991 and 1995. All tumors were diagnosed as cervical squamous cell carcinomas. Patient age and tumor staging are presented in Table 1. The tumors were staged based on clinical and histologic assessment according to the International Federation of Gynaecology and Obstetrics (FIGO) (Commentary; revised FIGO staging for gynecological cancer, 1989). Consecutive sections were cut from all formalin fixed, paraffin embedded samples. The tissue sections were used for DNA-ploidy measurements (thickness 8 $\mu$m), immunohistochemistry (4 $\mu$m) and tumor DNA extraction (50 $\mu$m). The last section (4 $\mu$m) was stained with hematoxylin/eosin for confirmation of the presence of tumor tissue. All tumor samples were obtained from patients before any clinical treatment, such as radiation therapy, which might introduce chromosomal abnormalities as a result of that treatment.

DNA cytometry

Figure 4A:
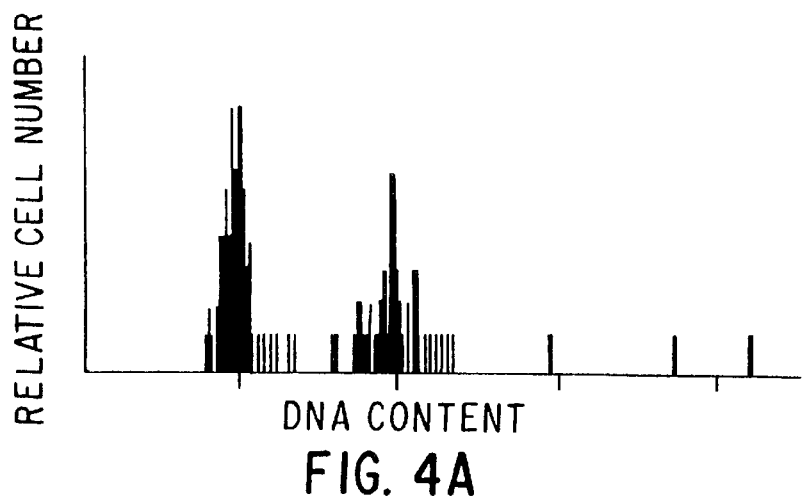
FIG. 4 shows examples of tetraploid (FIG. 4A), aneuploid/proliferating tetraploid (FIG. 4B), and aneuploid (FIG. 4C) DNA content histograms.
Figure 4B:
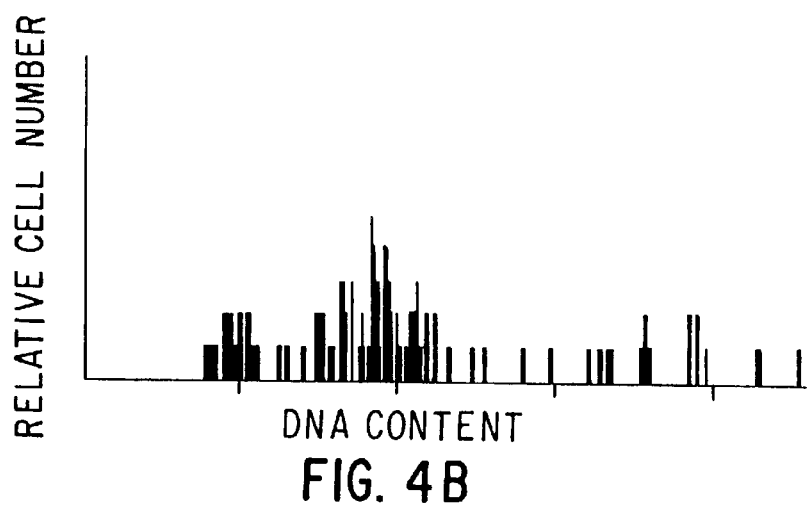
Figure 4C:
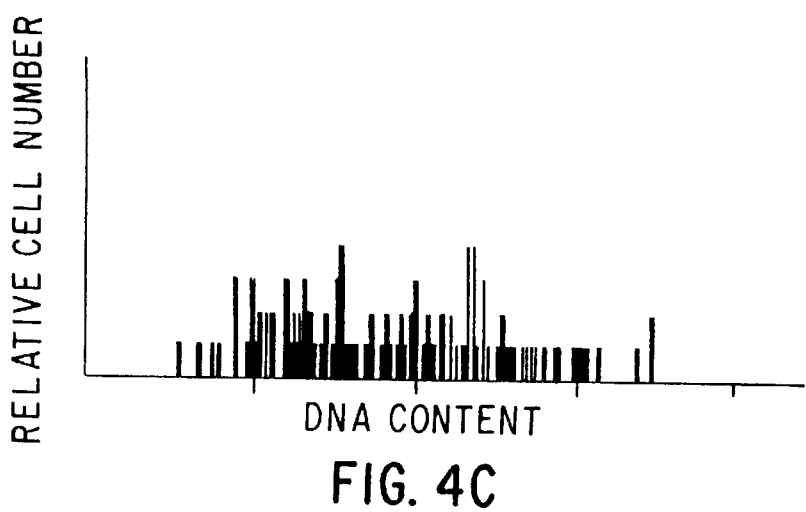

DNA content measurements were performed by image cytometry on Feulgen stained histologic sections as described (Auer et al. (1994) "The relationship between aneuploidy and p53 overexpression during genesis of colorectal adenocarcinomas" Virchows Archiv 424:343–347). All DNA values were expressed in relation to the corresponding staining controls, which were given the value 2c, indicating the normal diploid DNA content. Three classes of histograms were obtained: (i) tetraploid cases with a main peak in the 4c region and no cells or only a minor fraction of cells (<5%) exceeding 5c, (ii) aneuploid/proliferating tetraploid cases with a peak in the 4c region and a fraction of 5–20% of the cells exceeding 5c, and (iii) aneuploid cases with a main peak around the 4c region and more than 20% of the cells exceeding 5c. Examples of the histograms are shown in FIG. 4.

TABLE 1

Summary of the clinical data, the results from Mib-1, DO-1, WAF-1 staining, DNA ploidy measurements, HPY-genotyping and CGH in advanced cervical carcinomas. MIB-1, DO-1 and WAF-1 immunohistochemical results are presented as percentages of the tumor cells that reacted with the respective antibody. DNA histograms are classified as tetraploid (T), aneuploid/proliferating tetraploid (A/pT) and aneuploid (A) (see also FIG. 1). The HPV-types are provided as determined by dot blot analysis, neg.: negative for detection of HPV sequences. The CGH column shows the chromosomal aberrations detected in individual cases.

| case No. | list No. | patient age | tumor stage | MIB1 (Ki-67) % | DO1 (p53) % | WAF1/ p21 % | DNA | HPV | CGH |
|---|---|---|---|---|---|---|---|---|---|
| 1 | C1 | 69 | IIIb | 100 | neg. | <2 | 6.6c, A | 45 | −2q36-ter,−3p21-12,+3q26.1-ter,++5p,−5q35-ter,−6q, −8pter-22,++8q,−11q,−13q11-14,−X |
| 2 | C3 | 84 | IIIb | 40 | 20 | 50 | 2.8c, A | 16 | +1q,+3(++3q26−27),−5pter-14,+7,++8,−9pter-21,−14q31-ter,−X |
| 3 | C6 | 46 | IIb | 90 | neg. | 60 | 3.6c, A/pT | 16 | −2q34-ter,+3q25-ter,−6q25-ter,++9pter-23,−11q22-ter, +Xpter-q13 |
| 4 | C7 | 50 | IIIb | 90 | 20 | 40 | 5.1c, A | 39 | +1q,+2p,+3q21-ter,−4p15-qter,+5p,+5q31-ter,+6p,+9q,+12p, +12q23-ter,+13q31-ter,−14q22-24, +15q24-25,+16,+17p,++17q,+19q,+20p,++20q,+22 |
| 5 | C8 | 36 | IIb | 90 | <2 | 10 | 8.0c, A/pT | 45 | +1q,−2q36-ter,+3q,−4pter-q23,−4q34-ter,+5p,−5q14-23,+6p, ++11q22-23,+16,−22,+Xp |
| 6 | C9 | 87 | IIIb | 80 | 10 | 40 | 5.8c, A | 31 | +1,−2q36-ter,−10q26-ter,+12,+14q24-ter,+15,−18q23-ter,+Xq |
| 7 | C11 | 72 | IIIb | 90 | 10 | 30 | 4.1c, A/pT | 16 | +1q,+3q,++12p13 |
| 8 | C13 | 42 | IIIb | 80 | <2 | 30 | 6.1c,A | 45 | −8pter-23 |
| 9 | C15 | 74 | IIIb | 70 | <2 | 30 | 4.3c, A/pT | 16 | +1q,−3p,+3q,−8p,+15 |
| 10 | C16 | 71 | IIIb | 90 | neg. | 10 | 3.8c, A | 33 | −3pter−q21,+3q22-ter,+5q,−8p,+8q,−11q14-ter,−14,−16q,++20p,−X |
| 11 | C18 | 67 | IIb | 60 | 60 | 60 | 5.2c, A | neg. | +6p,+6q21-22,++19q,+20p,++20q,+Xpter-q13 |
| 12 | C19 | 62 | IIb | 50 | 20 | 50 | 3.8c, T | neg. | +3q |

TABLE 1-continued

Summary of the clinical data, the results from Mib-1, DO-1, WAF-1 staining, DNA ploidy measurements, HPY-genotyping and CGH in advanced cervical carcinomas. MIB-1, DO-1 and WAF-1 immunohistochemical results are presented as percentages of the tumor cells that reacted with the respective antibody. DNA histograms are classified as tetraploid (T), aneuploid/proliferating tetraploid (A/pT) and aneuploid (A) (see also FIG. 1). The HPV-types are provided as determined by dot blot analysis, neg.: negative for detection of HPV sequences. The CGH column shows the chromosomal aberrations detected in individual cases.

| case No. | list No. | patient age | tumor stage | MIB1 (Ki-67) % | DO1 (p53) % | WAF1/ p21 % | DNA | HPV | CGH |
|---|---|---|---|---|---|---|---|---|---|
| 13 | C20 | 38 | IIb | 90 | neg. | neg. | 4.0c, A/pT | 45 | −3p,−4,++5p,−5q11−23,+6pter−21,−9p,+12q,+13q32−ter,−14,−17p,+17q,+19q13.2−ter,−X |
| 14 | C21 | 36 | IIIb | 50 | neg. | 70 | 4.0c, T | 16 | −3p,+3q,−4,−10,−11pter−15,−11q22−ter |
| 15 | C22 | 74 | IIb | 80 | <2 | 60 | 4.0c, T | 16 | +1,−3p,+3q,++5p,+6p,−6q,++9pter−24,−13,+X |
| 16 | C23 | 58 | IIb | 50 | 20 | 50 | 3.6c, T | 16 | +1q,−2q36−ter,−3p,+3q(++3q24−ter),−6q,−7q21−ter,+9,−10q |
| 17 | C24 | 46 | IV | 90 | neg. | 60 | 4.2c, A/pT | 16 | −2pter−24,−2q32−ter,−3p21−11,+3q,−4,−13,+14 |
| 18 | C26 | 75 | IIb | 60 | 10 | 40 | 3.8c, A/pT | neg. | +1q,−6,−14,−Xq21−ter |
| 19 | C27 | 87 | IIIb | 60 | neg. | 70 | 4.0c, A/pT | neg. | +1,+2p,−3p,+3q,−5p,−9p,+X |
| 20 | C29 | 72 | IVa | 20 | 80 | 60 | 4.1c, A/pT | neg. | +1q,−2q22−ter,−3p,+3q24−ter,−4q,−8p,+8q,−17p,−18q,−21 |
| 21 | C30 | 81 | IIIb | 90 | neg. | 40 | 3.8c, A/pT | 31 | +1q,−2q36−ter,−3p21−11,+3q23−ter,−4q,−6p,−6q26−ter,−9p,−10p,−11pter−14,+11p13−q13,−11q14−ter,−13,−17pter,−12,−18,+Xq22−24 |
| 22 | C31 | 63 | IVa | 80 | neg. | 80 | 5.0c, A | 52 | ++3q21−ter,−4p,++5pter−13,+6,−8p,+8q,+9,++12p,+12q,−13q14−22,+18,+20,+22 |
| 23 | C32 | 79 | IIIb | 90 | 10 | 20 | n.d. | 18 | +1,+3q,+6,+8,+9,+10,++14,+15,+16,+17q,−18q,+19,+20,+21 |
| 24 | C33 | 64 | IIb | 80 | neg. | 50 | 4.1c, A/pT | 45 | −3p,+3q,+4q21−22,−6,−13,+15q21−25 |
| 25 | C34 | 51 | IIIb | 80 | 5 | 30 | 7.0c, A/pT | 16 | +5p,+9q,−12p,+12q,−X |
| 26 | C36 | 54 | IIb | 90 | 5 | 70 | 6.7c, A/pT | 16 | +1q,+3q21−ter,+6pter−12,+9p,+17 |
| 27 | C37 | 84 | IIb | 80 | neg. | 70 | 4.6c, A/pT | 35 | −2q34−ter,3p,+3q,−6,−9p,−14q21−23,+15q22−25,−17p,+20 |
| 28 | C39 | 34 | IIb | 60 | neg. | 70 | 4.0c, T | 45 | −3p,−4p,+5p,−5q33−ter,−13 |
| 29 | C40 | 50 | IIIa | 90 | 5 | 30 | 5.2c, A | 16 | +3q21−ter,+19q |
| 30 | C42 | 81 | IIIb | 90 | <2 | 50 | 6.2c, A | 16 | −2q,−3p,++3q,−4q,++5p,+5q,−8pter−23,−9p,−10p,−11,−12p,−13,+14q22−ter,+17,+19,+20 |

Immunohistochemistry

Proliferative activity was determined with an antibody (MIB-1) directed against the Ki-67 antigen. The antibody distinguishes cells in G0 from cells that are in G1-S-G2-M phase of the cell cycle. p21WAF-1 expression was analyzed with the WAF-1 antibody (Oncogene Sciences), and TP53 expression was determined with the DO-1 antibody (Santa Cruz). Immunohistochemistry was performed essentially as described (Steinbeck et al. (1995) "The relationship between proliferating cell nuclear antigen (PCNA), nuclear DNA content and mutant p53 during genesis of cervical carcinoma" Acta Oncol 34:171–175). The quantification of the results is presented in Table 1.

HPV genotyping

HPV genomes in the purified DNA samples were identified by PCR, with the MY09-MY11 L1 consensus primers used for amplification (Bosch et al. (1995) "Prevalence of human papilloma virus in cervical cancer: a worldwide perspective" J Natl Cancer Inst 87:796–802). 25 type-specific probes and one generic HPV probe were used to diagnose the HPV type in the PCR products (Hildesheim et al. (1994) "Persistence of type specific human papilloma virus infection among cytologically normal women" J Infect Dis 169:235–240). β-globin amplification was used as a positive control for evaluation of the adequacy of tumor DNA.

CGH analysis was performed as follows and as described above. Tumor DNA was prepared from the formalin fixed, paraffin embedded samples. Prior to DNA extraction, the paraffin was removed manually as completely as possible. The tissue was cut into small pieces, and remainders of paraffin were removed by incubation in xylene (45° C. for 15 min.), followed by one washing step in ethanol. After centrifugation, the samples were dried by centrifugation under vacuum. The samples were resuspended in 1 ml sodium isothiocyanate (1 M) and incubated at 37° C. overnight. The tissue was washed and resuspended in 400 µl DNA isolation buffer (75 mM NaCl, 25 mM EDTA, and 0.5% Tween 20®). Proteinase K was added to a final concentration of 1 mg/ml, and the tissue was incubated overnight at 55° C. The DNA was then subjected to two phenol extraction steps, one wash in chloroform:isoamyl alcohol [24:1 (v/v)], ethanol precipitated, and resuspended in sterile water. Nick translation was performed with bio-16-dUTP (tumor DNA) and digoxigenin-11-dUTP (reference DNA, prepared from a karyotypically normal female donor). Five hundred nanograms of each of the labeled genomes were combined and hybridized with an excess of Cot-1 DNA (25 µg) to metaphase chromosomes prepared from a karyotypically normal donor. The biotin-labeled tumor genome was visualized with avidin conjugated to FITC (Vector Laboratories), and the digoxigenin-labeled reference DNA with a mouse anti-digoxin antibody (Sigma, St. Louis, Mo.), followed by detection with a goat anti-mouse antibody conjugated to TRITC (Sigma). Chromosomes were counterstained with DAPI to generate a G-like banding pattern. Gray scale images of the DAPI counterstain, the FITC (Fluorescein Isothiocyanate) labeled tumor DNA, and the Tetramethylrhodamine B Isothiocyanate (TRITC)-labeled reference DNA from at least 8 metaphases from each hybridization were acquired with a cooled CCD camera (CH250, Photometrics, Tucson, Ariz.) connected to a Leica DMRBE microscope equipped with fluorochrome specific optical filters TR1, TR2, and TR3 (Chroma Technology, Brattleboro, Vt.). Quantitative evaluation of the hybridization was achieved with a custom designed computer program, the details of which are described by du Manoir et al. ("Quantification of comparative genomic hybridization" Cytometry 19:27–41 (1995)). Average ratio profiles were used to identify chromosomal copy number changes in all cases.

Results

The previous study identified a gain of chromosome arm 3q as a recurrent chromosomal aberration that occurs at the transition from preinvasive to invasive, early-stage cervical carcinomas. The present study was undertaken to address the question whether gain of 3q is maintained when the tumors progress, and to identify additional chromosomal aberrations, if any, that may be required for further progression of cervical carcinomas. This present study discloses the mapping of chromosomal gains and losses in 30 cases of advanced stage cervical carcinomas. The clinical data are summarized in Table 1.

CGH analysis

Genomic tumor DNA was extracted from 50 µm formalin-fixed, paraffin embedded tissue sections that were microdissected from representative regions of the tumor. Average ratio profiles were used for mapping of copy number changes in all instances. Chromosomal aberrations were detected in all 30 cases; the average number of chromosomal aberrations per case was 8.2. Despite the high number of chromosomal aberrations, a recurrent and specific pattern emerged in advanced-stage cervical carcinomas: the most frequent copy number alteration was a gain of chromosome arm 3q, which occurred in 23 of the 30 cases (77%). In four cases, the gain of 3q was present as a high level copy number increase (amplification). The consensus region of 3q amplification was mapped to chromosome bands 3q26–27. Gain of genetic material was also identified on chromosome arms 1q (14/30), 5p (9/30), 6p (8/30), and 20p (7/30). Whole-arm amplifications were frequently observed on 5p. Regional high-level copy number increases (amplifications) were mapped to chromosome bands 3q26–27, 9p23–24, 11q22–23, and 12p13. The most common chromosomal copy number decrease was mapped to chromosome arm 3p (15/30), band 2q36–37 (10/30), 6q (8/30), 8p (7/30), and 13q (8/30). A summary of chromosomal gains and losses is presented in FIG. 5.

HPV genotyping

The presence of HPV genomes was analyzed by PCR in the same DNA as for CGH. All samples could be analyzed successfully with a primer for the β-globin gene used as a control. HPV genomes were not detected in 5 cases. Twenty-five tumor samples yielded positive test results. HPV 16 accounted for 48% of the infections, followed by HPV 45 (6/25). (Table 1).

DNA ploidy measurement

DNA ploidy was measured on consecutive tissue sections by image cytometry. Image cytometry complements the CGH-analyses by providing information of the DNA ploidy that cannot be gained from CGH-experiments alone. One of the tumors showed a normal diploid DNA content. Most cases had crude aneuploidy, with either proliferating tetraploid cell populations or highly aneuploid cell populations; more than 20% of the cells exceeded 5c values. (Table 1).

Immunocytochemistry

The antibodies MIB-1, which is directed against the Ki-67 antigen, DO-1, which reacts with TP53, and p21 WAF1, which binds to the p53-activated cell cycle regulator WAF1, were used for immunohistochemical staining of consecutive tissue sections. Proliferative activity was, in general, markedly increased, with most tumor samples showing strong reactivity in 70–90% of the cells. With the exception of two cases (11 and 20), immunoreactivity with DO-1 (directed against TP53) was negative or only slightly increased. Immunoreactivity for p21/WAF1 was generally elevated. The strong expression of TP53 in cases 11 (60% of the cells reacting) and 20 (80%) did not affect the expression pattern of WAF-1. (Table 1).

This study summarizes the results of a combined phenotype/genotype analysis of 30 cases of advanced-stage cervical carcinomas. By using CGH as a molecular cytogenetic screening test for copy number changes, this study has identified a recurrent and stage-specific pattern of chromosomal aberrations in these tumors. Proliferation analysis and measurement of the cellular DNA content has revealed that advanced-stage cervical tumors were highly proliferative and aneuploid, frequently with stemlines in the tetraploid region. The expression status of TP53 and p21/WAF1 was examined to understand the involvement of p53 in the progression of cervical carcinomas. High-risk HPV types were detected in 85% of the tumors.

CGH analysis uncovered a recurrent pattern of chromosomal aberrations in advanced-stage disease. Most commonly observed was a gain of chromosome arm 3q (23 of 30 tumors). In 4 cases, these gains were present as high-level copy number increases. The smallest amplicon could be mapped to chromosome bands 3q26–27. It is likely that this region harbors a gene or genes whose gain of function is important in cervical carcinogenesis. Other characteristic copy number increases were mapped to chromosome arm 5p, remarkably often as high-level copy number increases, and to chromosome 1q.

The DNA copy number changes that occur in the progression from normal cervical epithelium to stage I invasive carcinomas was previously studied. Nine of ten of the invasive carcinomas exhibited a gain of chromosome arm 3q, whereas this aberration was present in only 1 of 13 severe dysplasias. That data discloses for the first time that the gain of chromosome arm 3q occurs at the transition from preinvasive to invasive disease. This follow-up analysis of 30 cases of advanced-stage carcinomas shows that this particular chromosomal aberration was maintained in the majority of the tumors (77%). However, additional chromosomal changes emerged that include gains of chromosome arms 1q and 5p, as well as losses of 2q. The analyses allow us to identify a stage specific pattern of chromosomal aberrations, in which 3q gain is an early event that coincides with the progression from preinvasive lesions to stage I invasive carcinomas. The gains of chromosome arms 1q and 5p, however, exemplify genetic abnormality that correlate with advanced stages of tumor progression.

The correlation of phenotype/genotype in cervical carcinomas can be summarized as follows: HPV infection is present in mildly dysplastic lesions and persists throughout advanced stages. Virtually all HPVs in lesions with increased levels of dysplasia belong to the high-risk group. Proliferative activity reaches maximum levels in severely dysplastic lesions and remains elevated during the progression to advanced-stage tumors. The tetraploidization already observed in mild dysplasia is replaced by cells with profound aneuploidy. The gain of chromosome arm 3q is an early event in cervical carcinogenesis and occurs at the transition from premalignant lesions to invasive carcinoma, stage I. During progression to advanced-stage disease, additional chromosomal aberrations are acquired, including, the gain of chromosome arms 1q and 5p, as well as the loss of chromosome bands 2q36–37. The gain of chromosome 3q, however, persists.

What is claimed is:

1. A method of detecting the presence of invasive cervical carcinoma in a subject comprising detecting in a cervical cell from the subject the presence of at least one extra copy of at least a fragment of chromosome 3q; the presence of at least one extra copy of at least a fragment of chromosome 3*q* indicating the presence of invasive cervical carcinoma in the subject.

2. The method of claim 1, wherein the subject is a human.

3. The method of claim 1, wherein the detection occurs in situ.

4. A method of detecting the presence of advanced-stage cervical carcinoma in a subject comprising detecting in a cervical cell from the subject the presence of at least one extra copy of at least a fragment of chromosome 5*p*, 1*q*, 6*p*, 8*q*, 15*q*, 17*q*, or 20, or the loss of at least a fragment of chromosome 3*p*, 4*p*, 6*p*, 8*p*, or 13*q*; the presence of at least one extra copy of at least a fragment of chromosome 5*p*, 1*q*, 6*p*, 8*q*, 15*q*, 17*q*, or 20, or the loss of at least a fragment of chromosome 3*p*, 4*p*, 6*p*, 8*p*, or 13*q* indicating the presence of advanced-stage cervical carcinoma in the subject.

5. The method of claim 4, wherein the subject is a human.

6. The method of claim 4, wherein the detection occurs in situ.

7. A method of classifying dysplastic cervical cells as having progressed from non-invasive cervical carcinoma cells to an invasive cervical carcinoma in a subject comprising:

a) analyzing the dysplastic cervical cells for the presence of a chromosome abnormality which is associated with invasive cervical carcinoma, wherein the chromosome abnormality comprises the presence of at least one extra copy of at least a fragment of chromosome 3*q*; and b) classifying the dysplastic cervical cells having the chromosome abnormality as having progressed from a non-invasive cervical carcinoma cells to an invasive cervical carcinoma in the subject.

* * * * *

UNITED STATES PATENT AND TRADEMARK OFFICE
CERTIFICATE OF CORRECTION

PATENT NO. : 5,919,624
APPLICATION NO. : 08/781424
DATED : July 6, 1999
INVENTOR(S) : Thomas Ried et al.

Figure 5:
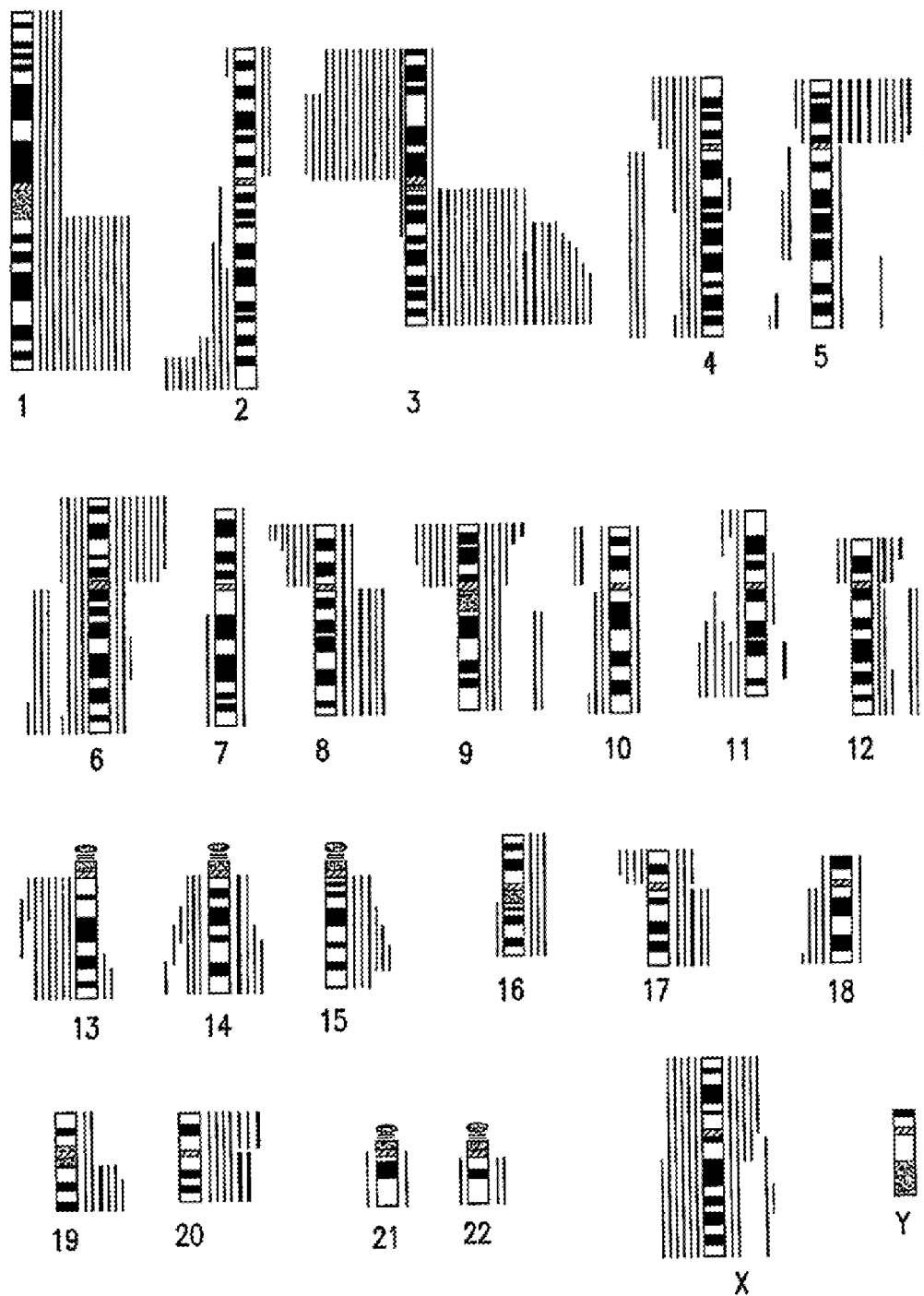
FIG. 5 shows karyograms of gains and losses in 30 cases of advanced-stage cervical carcinoma. Lines on the right side of the ideograms reflect copy number increases; lines on the left, represent copy number decreases. Heavy lines symbolize high-level copy number increases (amplifications).

It is certified that error appears in the above-identified patent and that said Letters Patent is hereby corrected as shown below:

Please insert Figure 5 which was inadvertently omitted from Submission of Formal Drawings, filed on January 18, 1999.

Signed and Sealed this

Eighteenth Day of September, 2007

JON W. DUDAS
*Director of the United States Patent and Trademark Office*